United States Patent [19]

Pelrine

[11] Patent Number: 5,105,039
[45] Date of Patent: Apr. 14, 1992

[54] PROCESS FOR PRODUCING LUBRICANT FLUIDS OF IMPROVED STABILITY

[75] Inventor: Bruce P. Pelrine, Trenton, N.J.

[73] Assignee: Mobil Oil Corporation, Fairfax, Va.

[21] Appl. No.: 693,255

[22] Filed: Apr. 29, 1991

[51] Int. Cl.$^5$ .............................................. C07C 5/393
[52] U.S. Cl. .................................. 585/407; 585/417
[58] Field of Search ................................ 585/417, 407

[56] References Cited

U.S. PATENT DOCUMENTS

| | | | |
|---|---|---|---|
| 3,756,942 | 9/1973 | Cattanach | 208/137 |
| 3,760,024 | 9/1973 | Cattanach | 260/673 |
| 4,169,865 | 10/1979 | Bamforth et al. | 585/314 |
| 4,720,602 | 1/1988 | Chu | 585/407 |
| 4,740,647 | 4/1988 | Hussmann et al. | 585/411 |
| 5,012,020 | 4/1991 | Jackson et al. | 585/12 |
| 5,015,795 | 5/1991 | Pelrine | 585/330 |
| 5,019,670 | 5/1991 | Le et al. | 585/467 |

*Primary Examiner*—Asok Pal
*Attorney, Agent, or Firm*—Alexander J. McKillop; Charles J. Speciale; Malcolm D. Keen

[57] ABSTRACT

The stability of HVI-PAO olefin oligomers is improved by reaction of the oligomer over an acidic function catalyst which introduces aromatic groups into the oligomer by cracking a portion of the oligomer to form cracking fragments which are then aromatized to aromatics which are subsequently alkylated by the oligomer. This reaction incorporates an aromatic function into the oligomer to produce a modified oligomer product of improved stability. The olefinic oligomers are prepared from 1-alkene by oligomerization in contact with a reduced metal oxide, preferably reduced chromium oxide, catalyst on support such as silica. The products retain the unique features of the olefin oligomer and exhibit high viscosity index and low pour point as well as improved thermal and oxidative stability and additive solvency characteristics resulting from the introduction of aromatic moieties into the structure of the oligomer by the intramolecular dehydrocyclization reaction.

25 Claims, 2 Drawing Sheets

PROCESS FOR PRODUCING LUBRICANT FLUIDS OF IMPROVED STABILITY

CROSS REFERENCE TO RELATED APPLICATIONS

This application is related to the following applications:
Ser. No. 07/345,606, filed May 1, 1989, now U.S. Pat. No. 5,012,020,
Ser. No. 07/562,179, filed Aug. 3, 1990, now U.S. Pat. No. 5,015,795,
Ser. No. 07/629,946, filed Dec. 19, 1990,
Ser. No. 07/515,030, filed Apr. 26, 1990, now U.S. Pat. No. 5,019,670,
Ser. No. 07/344,935, filed Apr. 28, 1989,
Ser. No. 07/693,161, filed concurrently.

FIELD OF THE INVENTION

This invention relates to a process for producing alkylated aromatic compositions useful as lubricant basestock and lubricant additives. The invention also relates a process for producing lubricant compositions of high viscosity index (VI) and increased thermal stability by alkylating aromatics with high VI, low pour point poly-alpha-olefin oligomers.

BACKGROUND OF THE INVENTION

Efforts to improve upon the performance of natural mineral oil based lubricants by the synthesis of oligomeric hydrocarbon fluids have been the subject of important research and development in the petroleum industry for a large number of years and have led to the introduction of a number of superior polyalpha-olefin (PAO) synthetic lubricants produced by the oligomerization of alpha-olefins or 1-alkenes. In terms of lubricant property improvement, the thrust of the industrial research effort on synthetic lubricants has been toward fluids exhibiting useful viscosities over a wider range of temperature, i.e., improved viscosity index (VI), while also showing lubricity, thermal and oxidative stability and pour point equal to or better than mineral oil. These new synthetic lubricants exhibit lower friction characteristics and are therefore capable of increasing mechanical efficiency of various types of equipment including engines, transmissions, worm gears and traction drives, doing so over a wider range of operating conditions than mineral oil lubricants.

Notwithstanding their generally superior properties, PAO lubricants are often formulated with additives to enhance those properties for specific applications. Among the more commonly used additives are oxidation inhibitors, rust inhibitors, metal passivators, antiwear agents, extreme pressure additives, pour point depressants, detergent-dispersants, viscosity index (VI) improvers, foam inhibitors and the like. This aspect of lubricant technology is described in Kirk-Othmer "Encyclopedia of Chemical Technology", 3rd Edition, Vol. 14, pp. 477-526, to which reference is made for a description of the use of such additives.

Improvements in synthetic lubricant technology have resulted both from new additive developments intended to address deficiencies in the lubricant (oligomer) basestocks as well as from developments in new base fluid (oligomer). Recently, lubricant compositions (referred to in this specification as HVI-PAO) of remarkable high VI coupled with low pour point have been developed. These lubricant compositions are described in U.S. Pat. Nos. 4,827,064 and 4,827,063, to which reference is made for a detailed description of these lubricants, methods for their preparation and of their properties and uses. These HVI-PAO materials comprise polyalpha-olefin oligomers prepared by the use of a reduced metal oxide, preferably reduced chromium, oligomerization catalyst. The lubricant product is characterized by a branch ratio less than 0.19, indicating a high degree of linearity and pour point below $-15°$ C. In its as-synthesized form, the HVI-PAO oligomer has olefinic unsaturation associated with the last of the recurring monomer units in the structure and this can be removed by a simple hydrogenative treatment to produce a stabilized, fully saturated oligomer product. Lubricants produced by the process cover the full range of lubricant viscosities and exhibit a remarkably high VI and low pour point even at high viscosity. Products of higher viscosity can also be produced by operating the oligomerization process at lower temperatures, typically $-20°$ to $+90°$ C., and these high viscosity products are useful as lubricant additives, especially VI improvers for both mineral and synthetic oils, as described in copending application Ser. No. 07/345,606, filed May 1, 1989, now U.S. Pat. No. 5,012,020, to which reference is made for a description of these higher viscosity oligomers, their properties and uses and of the method by which they may be made.

The process for preparing the HVI-PAO lubricants comprises, as noted above, contacting a $C_6$-$C_{20}$ 1-alkene feedstock with reduced valence state chromium oxide catalyst on porous silica support under oligomerizing conditions in an oligomerization zone to produce the high viscosity, high VI liquid hydrocarbon lubricant with branch ratios less than 0.19 and pour points below $-15°$ C. The oligomerization temperature is typically maintained at a value between 90° and 250° C. to produce the lubricant viscosity products. By operating the oligomerization process at lower temperatures, however, higher viscosity materials may be produced and these materials may be used as viscosity index (VI) improvers for lubricants, both of mineral oil and synthetic origin, as described Ser. No. 07/345,606. These higher viscosity HVI-PAO products typically have viscosities between 725 and 15,000 cS at 100° C., corresponding to weight molecular weights from about 15,000 to 200,000 and number molecular weights from about 5,000 to about 50,000; carbon numbers for these molecular weights are from about $C_{30}$ to about $C_{10,000}$, with a preferred range from about $C_{30}$ to about $C_{5,000}$. Like the liquid lubricant oligomers, these higher molecular weight oligomers are characterized by high VI coupled with excellent low temperature fluidity properties including pour point for the liquid products.

The lower molecular weight oligomers used for the production of low viscosity lubricants, for example, lubricants in the 5-10 cS range, are produced at relatively high temperatures which lead to the production of significant amounts of the non-lubricant range dimer (about $C_{20}$ with decene as the starting olefin) as well by-products including isomerized olefin. Although the dimer may be reacted with the oligomer, as described in Ser. No. 07/562,179, filed Aug. 3, 1990, now U.S. Pat. No. 5,015,795, to improve the properies of the oligomer, the necessity of a separate fractionation and reaction steps renders this process somewhat less desirable than its potential would indicate.

The HVI-PAO oligomers have excellent fluid flow properties, as evidenced by their high VI values and low pour points but they do not necessarily possess the highest degree of thermal and oxidative stability under the most stringent conditions. For this reason, it would be desirable to improve their stability in these respects if this could be done without significant deterioration of their excellent rheological characteristics.

Alkylated aromatics, particularly alkylated naphthalene are known to possess good thermal and oxidative stability as disclosed in U.S. Pat. Nos. 4,211,665, 4,238,343, 4,604,491 and 4,714,7944 but these naphthalene derivatives do not usually possess good rheological properties: in particular, they have extremely poor VI, consonant with their aromatic character. In general, however, alkylated naphthalenes have been disappointing as lubricants although their good thermal and oxidative stability have made them suitable for use as transformer oils and heat exchange media. Efforts have therfore been made to combine the good thermal and oxidative stability of the aromatic materials with the excellent viscometric properties of the HVI-PAO oligomers by the introduction of aromatic moieties into the HVI-PAO molecules.

Co-pending application Ser. No. 07/629,946, filed Dec. 19, 1990, describes a method of improving the thermal and oxidative stability of the HVI-PAO oligomers by alkylating the unsaturated oligomer product with an aromatic compound such as benzene or naphthalene. The products have the enhanced stability and good solvency characteristics associated with the aromatic component while retaining the excellent rheological characteristics of the HVI-PAO oligomers. According to this method, the HVI-PAO oligomer is reacted with the aromatic compound in the presence of an alkylation catalyst such as a Lewis acid e.g. aluminum trichloride or boron trifluoride or a solid acidic zeolite such as zeolite Y.

Co-pending application Ser. No. 07/515,030, filed Apr. 26, 1990, now U.S. Pat. No. 5,019,670, describes a method for improving thermal and oxidative stability of HVI-PAO olefin oligomers by reaction with aromatic compounds such as naphthalene in the presence of the synthetic zeolite MCM-22. The products have enhanced stability while retaining the desirable viscometric characteristics of the original HVI-PAO staring material used as the alkylation agent in the reaction.

Co-pending application Ser. No. 07/344,935, filed Apr. 28, 1989, describes a method for improving the thermal and oxidative stability of HVI-PAO olefin oligomers by introducing aromatic moieties into the structure of the HVI-PAO by intramolecular cyclization and without the addition of extraneous sources of aromatic materials.

SUMMARY OF THE INVENTION

We have now found that the stability—thermal and oxidative—of the HVI-PAO oligomers may be improved by treatment of the olefin oligomer with a catalyst under conditions which are conducive to the introduction of aromatic moieties within the oligomer structure without the addition of extraneous sources of aromatic materials. The reaction is believed to proceed by a pathway in which a portion of the HVI-PAO structure is cracked to small fragments which then form aromatics which are then alkylated by the remaining, unhydrogenated HVI-PAO to incorporate an aromatic function into the backbone structure. The catalyst for the reaction is therefore chosen to have a structure which enables the long-chain olefin oligomer to participate in the alkylation reaction with the aromatics as well as promoting the aromatization of the short-chain olefins formed by the cracking reactions. According to the present invention, the reaction is preferably carried out in the presence of the solid acidic catalytic material, zeolite MCM-22.

The lube boiling range products of the reaction have been found to possess good thermal and oxidative stability as well as good additive solvency characteristics related to the presence of aromatic moieties in the oligomer molecule. In addition, the products retain the unique structurally-related features of the HVI-PAO olefinic oligomer and thereby exhibit an extraordinary combination of properties relating to high viscosity index and low pour point which makes them very useful as lubricant base stock.

DETAILED DESCRIPTION

HVI-PAO products of improved thermal and oxidative stability are produced by subjecting the HVI-PAO oligomer to an aromatization treatment over an acidic catalyst. The process is particularly applicable to the low viscosity HVI-PAO materials, for example, the 3-10 cS oligomers although it is also applicable to higher viscosity oligomers.

Olefin Oligomer

The olefin oligomers are produced from the oligomerization of 1-alkenes over a reduced metal oxide catalyst, usually reduced chromium oxide on a silica support. As oligomerized, these HVI-PAO oligomers are mixtures of dialkyl vinylidenic and 1,2 dialkyl or trialkyl mono-olefin oligomers. Oligomerization of the olefin feed with the reduced metal oxide catalysts leads to an oligomer which is substantially free of double bond isomerization and has a high degree of linearity. Conventional PAO, on the other hand, formed by oligomerization over Lewis acid catalysts such as $BF_3$ or $ALCl3$, are formed by a carbonium ion which, in turn, promotes isomerization of the olefinic bond and the formation of multiple isomers of lower linearity, as shown by their branch ratios of above 0.19, as compared to a ratio of 0.20 or higher for conventional PAO oligomers produced with Lewis acid catalysts.

Olefins suitable for use as starting material in the preparation of olefinic HVI-PAO oligomers useful as starting material in the present invention include those olefins containing from 2 to about 20 carbon atoms such as ethylene, propylene, 1-butene, 1-pentene, 1-hexene, 1-octene, 1-decene, 1-dodecene and 1-tetradecene and branched chain isomers such as 4-methyl-1-pentene. Also suitable for use are olefin-containing refinery feedstocks or effluents. However, the olefins used in this invention are preferably alpha olefinic as for example 1-hexene to 1-hexadecene and more preferably 1-octene to 1-tetradecene, or mixtures of such olefins.

In the oligomerization process, the olefin feed is contacted with the oligomerization catalyst to produce the desired oligomer product. In the preparation of the liquid hydrocarbons suitable as lubricant basestocks an alpha-olefin feedstock comprising olefins of 6 to 20 carbon atoms, or mixtures of such olefins, is contacted with the oligomerization catalyst under oligomerization conditions, at a reaction temperature between 90° to 250° C. dependent upon the desired product viscosity. The higher viscosity products are made at oligomerization temperatures from about −20° to about +90° C., with the exact temperature selected being dependent upon the viscosity desired in the product. Thus, in general, the oligomerization temperature may be from about −20° to about 250° C., depending upon the characteristics, especially the viscosity, desired for the product.

In each case, the catalyst comprises a reduced metal oxide on a porous, solid support. The oxide is derived from a metal of Group VIB, preferably chromium, as the catalytic component on a porous support. The catalyst may be activated by treatment including oxidation at a temperature of 200° C. to 900° C. in the presence of an oxidizing gas and then by treatment with a reducing agent at a temperature and for a time sufficient to reduce the metal to a lower valence state. The catalyst most preferred is a lower valence Group VIB metal oxide on a porous inert support. Preferred supports include silica, alumina, titania, silica alumina, magnesia and the like. The support material binds the metal oxide catalyst. Those porous substrates having a pore opening of at least 40 Å are preferred.

The support material usually has high surface area and large pore volumes with average pore size of 40 to about 350 Å. The high surface area are beneficial for supporting large amount of highly dispersive, active chromium metal centers and to give maximum efficiency of metal usage, resulting in very high activity catalyst. The support should have large average pore openings of at least 40 Å, with an average pore opening of 60 to 300 Å preferred. This large pore opening will not impose any diffusional restriction of the reactant and product to and away from the active catalytic metal centers, thus further optimizing the catalyst productivity. Also, for this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, $H_2$, $NH_3$, $H_2S$, $CS_2$, $CH_3SCH_3$, $CH_3SSCH_3$, metal alkyl containing compounds such as $R_3Al$, $R_3B, R_2Mg$, RLi, $R_2Zn$, where R is alkyl, alkoxy, aryl and the like. Preferred are CO or $H_2$ or metal alkyl containing compounds. Alternatively, the Group VIB metal may be applied to the substrate in reduced form, such as CrII compounds. The resultant catalyst is very active for oligomerizing olefins at a temperature range from below room temperature to about 250° C. at a pressure of 0.1 atmosphere to 5000 psi. Contact time of both the olefin and the catalyst can vary from one second to 24 hours. The catalyst can be used in a batch type reactor or in a fixed bed, continuous-flow reactor.

The support material may usually be added to a solution of the metal compounds, e.g., acetates or nitrates, etc., and the mixture is then mixed and dried at room temperature. The dry solid gel is purged with air at successively higher temperatures to about 600° for a period of about 16 to 20 hours. After this, the catalyst is cooled down under an inert atmosphere to a temperature of about 250° C. to 450° C. and a stream of reducing agent such as CO or $H_2$ is contacted therewith for a period to reduce the catalyst as indicated by a distinct color change from bright orange to bluish green. Typically, the catalyst is treated with an amount of CO equivalent to a two-fold stoichiometric excess to reduce the catalyst to a lower valence CrII state. Finally the catalyst is cooled down to room temperature and is ready for use.

Further descriptions of the catalyst, its preparation and its use in the production of the HVI-PAO oligomers are given in U.S. Pat. Nos. 4,482,064 and 4,482,073 as well as in applications Ser. Nos. 07/345,606, filed May 1, 1989, now U.S. Pat. No. 5,012,020, Ser. No. 07/562,179, filed Aug. 3, 1990, now U.S. Pat. No. 5,015,795, Ser. No. 07/629,946, filed Dec. 19, 1990, Ser. No. 07/515,030, filed Apr. 26, 1990, now U.S. Pat. No. 5,019,670, Ser. No. 07/344,935, filed Apr. 28, 1989.

The product oligomers have atactic molecular structure of mostly uniform head-to-tail connections with some head-to-head type connections in the structure. These low branch ratio oligomers have high viscosity indices at least about 15 to 20 units and typically 30–40 units higher than equivalent viscosity prior art oligomers, which regularly have higher branch ratios and correspondingly lower viscosity indices in the lubricant products. These low branch ratios are also correlated with the lour points of the lubricant products.

The branch ratios are defined as the ratios of $CH_3$ groups to $CH_2$ groups in the oligomers are calculated from the weight fractions of methyl groups obtained by infrared methods, published in Analytical Chemistry. Vol. 25, No. 10, p. 1466 (1953).

$$\text{Branch ratio} = \frac{\text{wt. fraction of methyl group}}{1 - (\text{wt fraction of methyl group})}$$

In general, the HVI-PAO oligomers have the following regular head-to-tail structure where n is preferably 0 to 17, terminating in olefinic unsaturation:

with some head-to-head connections. The as-synthesized HVI-PAO molecular structure generally has one double bond unsaturation.

The HVI-PAO process also produces a different dimer compared to the dimer produced by 1-alkene oligomerization with commercial types of catalyst such as $BF_3$ or $AlCl_3$. Typically, it has been found that a significant proportion of unhydrogenated dimerized 1-alkene has a vinylidenyl structure as follows:

where $R_1$ and $R_2$ are alkyl groups representing the residue from the head-to-tail addition of 1-alkene molecules. For example, 1-decene HVI-PAO dimer, which participates in the post-oligomerization reaction, has been found to contain only three major components, as determined by GC. Based on $C^{13}$ NMR analysis, the unhydrogenated components were found to be 8-eicosene, 9-eicosene, 2-octyldodecene and 9-methyl-8 or 9-methyl-9-nonadecene.

The liquid lubricant compositions produced by the oligomerization process at relatively high oligomerization temperatures e.g. between 90° and 250° C., comprise $C_{30}$-$C_{1300}$ hydrocarbons, with branch ratios of less than 0.19, weight average molecular weights between 300 and 45,000, number average molecular weights between 300 and 18,000. The molecular weight distribution of these oligomers is between 1 and 5 and the pour point of the liquid lubricants is below −15° C.

The HVI-PAO oligomers, in the broadest terms, have a weight average molecular weight between 280 and 450,000 and number average molecular weight between 280 and 180,000. Measured in carbon numbers, molecular weights range from $C_{20}$ to $C_{1300}O$ and viscosity up to 7500 cs at 100° C., with a preferred range $C_{30}$ to $C_{1000}$ and a viscosity of up to 1000 cs at 100° C. for lube base stock material. Molecular weight distributions (MWD), defined as the ratio of weight average molecular to number average molecular weight, range from 1.00 to 5, with a preferred range of 1.01 to 3 and a more preferred MWD of about 1.05 to 2.5. The viscosities of the olefinic HVI-PAO oligomers used in the present process will typically range from 1.5 cS to 7500 cS (measured at 100° C.).

Usually, the lubricant range oligomers are produced by varying the oligomerization temperature to yield lubricant viscosity range oligomers having weight average molecular weight between 420 and 45,000 and number average molecular weight between 420 and 18,000. Measured in carbon numbers, molecular weights range from $C_{30}$ to $C_{1300}$ and a viscosity up to 750 cs at 100° C., with a preferred range of $C_{30}$ to $C_{1000}$ and a viscosity of up to 500 cS at 100° C. Molecular weight distributions (MWD), defined as the ratio of weight average molecular to number average molecular weight, range from 1.00 to 5, with a preferred range of 1.01 to 3 and a more preferred MWD of about 1.05 to 2.5. Compared to conventional PAO derived from $BF_3$- or $AlCl_3$-catalyzed polymerization of 1-alkene, HVI-PAO has been found to have a higher proportion of higher molecular weight polymer molecules in the product.

The viscosities of the lubricant HVI-PAO oligomers measured at 100° C. range from 3 cS to 5000 cS. The viscosity index for the liquid polyalpha-olefins is approximately described by the following equation:

$$VI = 156.8 + 4.94 \times (V_{100°C.})^{0.5},$$

where $V_{100°C.}$ is the kinematic viscosity in centistokes measured at 100° C.

The higher viscosity oligomers produced at oligomerization temperatures below about 90° C. comprise hydrocarbons which have a branch ratio below 0.19 and a viscosity at 100° C. which is typically from 100 to 20,000 cS. The hydrocarbons typically have weight average molecular weights from 15,000 to 200,000 and number average molecular weights from 5,000 to 50,000 with a molecular weight distribution from about 1 to about 5. The viscosity index of the liquid compositions of this type is at least 130 and usually higher, for example, above 180 or even 200 or higher. The high viscosity materials are characterized by high shear stability, being stable under high temperature, high shear rate conditions, notably at 150° C. and a shear rate of one million ($10^6$) reciprocal seconds. Reference is made to Ser. No. 07/345,606 for a more detailed description of these oligomers, their properties and uses as well of the methods by which they may be made.

As oligomerized, the HVI-PAO oligomers are mixtures of dialkyl vinylidenic and 1,2 dialkyl or trialkyl mono-olefins and the lower molecular weight unsaturated oligomers are usually hydrogenated to produce the thermally and oxidatively stable lubricants after removal of the non-lube boiling range fraction (dimer and lower) by distillation. In the present process, however, the oligomerization mixture is treated with an acidic catalyst to improve the stability of the product.

Post-Oligomerization Treatment

In the present process, the thermal and oxidative stabilities and solvency characteristics of the oligomers are improved by treatment under appropriate conditions with an acidic heterogeneous phase catalyst which can be readily separated from the reaction mixture by filtration or other mechanical means. The catalyst is one which promotes the desired cracking of the oligomer to provide olefin fragments which can then be converted to aromatics and the aromatics alkylated by the same catalytic material. The preferred catalyst for this purpose is the catalytic material MCM-22, which is described in U.S. Pat. No. 4,954,325, to which reference is made for a description of this zeolite, its properties and its preparation. This material may be defined by reference to its X-Ray diffraction patterns, as set out below. In its preferred form for use in the present process, the catalyst contains no metal component i.e. no component possessing hydrogenation-dehydrogenation activity.

Catalyst

In its calcined form, the synthetic porous crystalline component of the catalyst is characterized by an X-ray diffraction pattern including the lines shown in Table 1 below:

TABLE 1

| Interplanar d-Spacing (A) | Relative Intensity, $I/I_o \times 100$ |
| --- | --- |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, it may be characterized by an X-ray diffraction pattern in its calcined form including the following lines shown in Table 2 below:

TABLE 2

| Interplanar d-Spacing (A) | Relative Intensity, $I/I_o \times 100$ |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |

TABLE 2-continued

| Interplanar d-Spacing (A) | Relative Intensity, I/I₀ × 100 |
|---|---|
| 3.42 ± 0.06 | VS |

More specifically, the calcined form may be characterized by an X-ray diffraction pattern including the following lines shown in Table 3 below:

TABLE 3

| Interplanar d-Spacing (A) | Relative Intensity, I/I₀ × 100 |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines shown in Table 4 below:

TABLE 4

| Interplanar d-Spacing (A) | Relative Intensity, I/I₀ × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values are determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/I₀, where I₀ is the intensity of the strongest line or peak, and d (obs.) the interplanar spacing in Angstrom Units (Å), corresponding to the recorded lines, were determined. In Tables 1–4, the relative intensities are given in terms of the symbols W=weak, M=medium, S=strong, VS=very strong. In terms of intensities, these may be generally designated as follows:

| W = | 0–20 |
| M = | 20–40 |
| S = | 40–60 |
| VS = | 60–100 |

These X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, to which reference is made for a description of this material as well as of its preparation. Another crystalline material of this type is the preferred MCM-22.

MCM-22 is described in U.S. Pat. No. 4,954,325, to which reference is made for a description of this zeoite, its preparation and properties. The zeolite has a chemical composition expressed by the molar relationship:

$$X_2O_3:(n)YO_2,$$

where X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, MCM-22 has a formula, on an anhydrous basis and in terms of moles of oxides per n moles of YO₂, as follows:

$$(0.005-0.1)Na_2O:(1-4)R:X_2O_3:nYO_2$$

where R is an organic component. The Na and R components are associated with the zeolite as a result of their presence during crystallization, and are easily removed by the post-crystallization methods described in U.S. Pat. No. 4,954,325.

MCM-22 is thermally stable and exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the catalyst without having to first undergo an exchange step. To the extent desired, however, the original sodium cations of the as-synthesized material can be replaced by established techniques including ion exchange with other cations. Preferred replacement cations include metal ions, hydrogen ions, hydrogen precursor ions, e.g., ammonium and mixtures of such ions.

In its calcined form, MCM-22 appears to be made up of a single crystal phase with little or no detectable impurity crystal phases and has an X-ray diffraction pattern including the lines listed in above Tables 1–4.

Prior to its use as the catalyst in the present process, the crystals should be subjected to thermal treatment to remove part or all of any organic constituent present in the as-synthesised material.

The zeolite in its as-synthesised form contains organic cations as well as when it is in its ammonium form, can be converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to a limit imposed by the irreversible thermal degradation of the crystalline structure of the zeolite, typically up to about 925° C.

Prior to its use in the process, the zeolite crystals should be dehydrated, at least partially. This can be done by heating the crystals to a temperature in the range of from about 200° C. to about 595° C. in an atmosphere such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Treatment Conditions

In the present process, the unhydrogenated HVI-PAO lubricant fraction is reacted over the catalyst in the absence of any added aromatic under appropriate reaction conditions for the resulting modified HVI-PAO to contain aromatics formed from the HVI-PAO. It is believed that a portion of the HVI-PAO structure is cracked to small fragments which then form aromatics which are then alkylated by the remaining, unhydrogenated HVI-PAO to incorporate an aromatic function into the backbone structure. Sufficient aromaticity may be incorporated into the backbone to provide for increased stability and additive solvency. Since the degree of unsaturation of the resulting product is reduced, as measured by bromine number, the necessity for a hydrogenation step is eliminated. Bromine numbers are effectively reduced to 5 and below. The ability to elimnate the hydrogenation, which would normally follow the oligomerization step, is also desirable because it enables other product quality improvements to be effected. Hydrogenation converts any long chain olefins in the oligomerization efluent to long chain alkanes e.g. eicosene to eicosane, and because the long chain alkanes tend to have lower solidification points than the corresponding alkenes, any residual long chain alkenes in the oligomerization effluent are converted to the corresponding alkanes which, unless removed in a subsequent fractionation, give rise to pour and cloud point problems. The elimination of the hydrogenation reduces the magnitude of this potential problem.

The parent unhydrogenated HVI-PAO oligomer mixtures constituting the undistilled oligomerization product contain isomerized olefins and olefin dimers outside the lube boiling range (usually about 550°+F. (about 290° C.+), usually from 650°+to about 1050° F. (about 315° to about 565° C.)). This mixture represents a crude mixture which may be cascaded as the total effluent from the oligomerization process to a reactor containing the zeolite catalyst MCM-22 where the aromatized, thermally stable HVI-PAO is formed. The dimers and isomerized olefins present in the mixture may contribute to the stability of the reaction product by reaction with the oligomer in the presence of the catalyst to form higher molecular weight products, as described in co-pending application Ser. No. 07/693,161, filed concurrently.

The reaction is suitably effected at a temperature of between about 100° C. about 400° C., and preferably between about 150° C. and about 300° C., e.g. 250° C. Although relatively high temperatures of about 500° C. are favorable to the cracking reactions and the conversion of the cracking fragments to aromatics, somewhat lower temperatures typically below about 350° C. are preferred in the present instance in order to avoid excessive cracking of the oligomer. The reaction generally takes place at sufficient pressure to maintain the reactants in the liquid phase, normally at pressures of from about 0 to about 2000 psig (100 to about 13,890 kpa abs.) and preferably at not more than about 100 psig (about 790 kPa abs) for convenience. Pressure is favorable to aromatization of the cracking fragments and to the retention of light olefins so that the yields of the alkylated aromatic product increase with pressure. Reaction time is typically from about 0.5 to 24 hours. Feed/catalyst ratios are typically between 0.1 to 10 (by weight).

The reaction can be carried out as a batch-type process or in a semi-continuous or continuous operation sutiably utilizing a fixed bed catalyst system.

Products

The products of the process which, as stated above, are believed to be aromatized HVI-PAO materials of improved thermal and oxidative stability and improved additive solvency characteristics, are useful as lubricant basestock and as additives for both mineral and synthetic lubricants. The higher molecular weight products are especially useful as multipurpose lubricant additives since they have excellent VI improvement properties which may be combined with other valuable additive characteristics. The introduction of the aromatic moiety into the HVI-PAO increases thermal stability, increases solubilizing power of the product and may add other properties useful in additives such as antiwear properties and VI enhancement. Therefore, as additives, their usefulness is compounded to incorporate in a single additive product the capability to improve a lube basestock thermal stability, VI, solvency and seal swelling power as well as improving antiwear characteristics. They possess the further advantage of great flexibility in the range of viscosity in which they can be prepared so that their additive properties can be used in a viscosity compatible with the viscosity formulation of the lube basestock.

EXAMPLES 1-2

Two different viscosity grades of modified HVI-PAO were made by the reaction over MCM-22 of two samples of HVI-PAO. One product was a medium viscosity (52 cS) material and the other of high viscosity (109 cS).

The medium viscosity product (52 cS) product was made from a HVI-PAO having a viscosity of 39 cS and the high viscosity product (109 cS) from a HVI-PAO of 90 cS viscosity. The crude HVI-PAO starting materials were synthesized according to the method of U.S. Pat. No. 4,4827,064 or U.S. Pat. No. 4,827,073, using a reduced Cr(II) on silica catalyst at temperatures of 150° C. for the medium viscosity material and 125° C. for the high viscosity material. The crude HVI-PAO usually contains unreacted 1-decene, isomerized decenes, $C_{20}$ olefins (dimer) as well as $C_{30}$ and higher decene oligomers, with the relative quantity of the higher oligomers increasing with the viscosity of the oligomer.

The modified HVI-PAO materials were made by a batch-type reaction of the starting oligomerization mixture, without preliminary distillation to separate the non-lube range materials i.e. products below the trimer ($C_{30}$). The reaction was carried out over the MCM-22 catalyst under the conditions shown in Table 6 below. The catalyst properties are shown in Table 5.

The product properties are shown in Table 6. The incorporation of aromatics into HVI-PAO structures, tends to increase the product viscosity while decreasing the viscosity index: at equivalent viscosities of 52 cS and 109 cS (100° C.), an untreated HVI-PAO would have viscosity indices of 192 and 208. The amount of aromatics incorporated into the structure of the two modified HVI-PAO's were determined by proton NMR. The thermal stability results for both products were determined by subjecting the products to 300° C. for 24 hours. At the end of this period, the resulting viscosities were measured (at 100° C.) and compared to the initial viscosities. The percentage loss was then calculated. From Table 6 it can be seen that the medium viscosity material loss 11%, while the high viscosity material loss was 19%, representing an improvement in both cases when compared to untreated HVI-PAO.

TABLE 5
MCM-22 Properties

| | |
|---|---|
| Surface area, BET, $m^2 \cdot g^{-1}$ | 494 |
| $SiO_2/Al_2O_3$ | 25 |
| Alpha | 215 |
| n-Hexane abs., wt. pct. | 14.2 |
| $H_2O$ abs., wt. pct. | 17.0 |
| Morphology | Platelet |

TABLE 6
MCM-22 Modified HVI-PAO

| Example No. | 1 | 2 |
|---|---|---|
| HVI-PAO, g. | 45 | 45 |
| Decenes, g. | 2.5 | 2.5 |
| Dimers, g. | 2.5 | 2.5 |
| MCM-22, g. | 2.0 | 2.0 |
| Temp., °C. | 250 | 250 |
| Reaction time, hrs. | 18 | 18 |
| Yield, wt. pct. | 85 | 85 |
| Visc. 40° C., cS | 489 | 1106 |
| Visc. 100° C., cS | 52 | 109 |
| VI | 168 | 194 |
| Aromatics, wt. pct. | 5 | 5 |
| Stability, visc. loss, wt. pct. | 11 | 19 |

Figure 1:
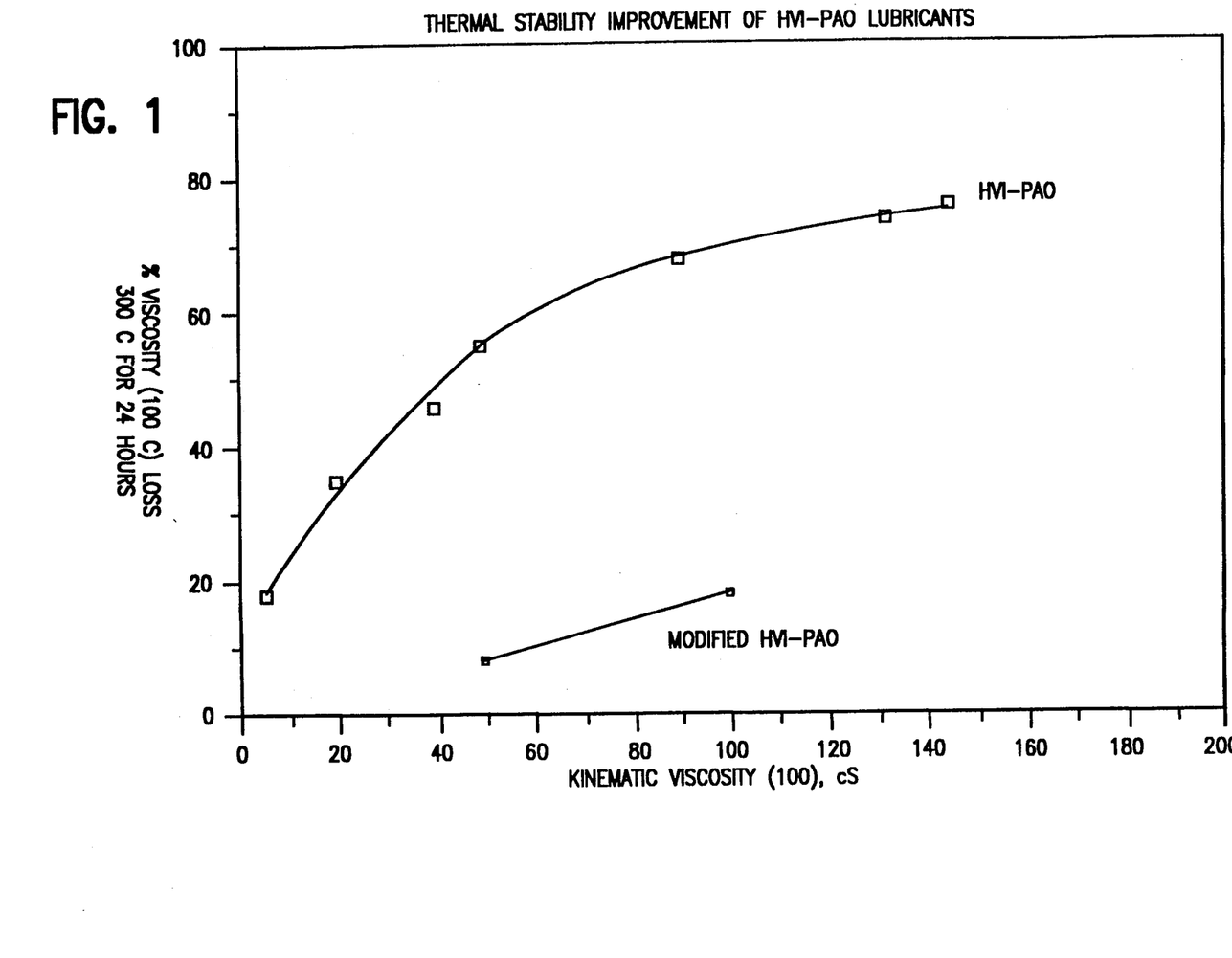
FIG. 1 is a graph showing the improvement in stability with the modified HVI-PAOs relative to an untreated HVI-PAO.

The improvement in stability relative to an untreated HVI-PAO is also shown graphically in FIG. 1. Untreated HVI-PAO's, with viscosities which range from about 5 cS to 145 cS, are seen with their respective percentage viscosity losses in the same test. For a 145 cS HVI-PAO, the loss is around 75 percent. Generally, the loss in viscosity increases as the viscosity of the HVI-PAO increases. The viscosity losses for the modified HVI-PAO are also shown: a substantial improvement in thermal stability is afforded by the present treatment process. For a 52 cS modified HVI-PAO, the loss is about 11 percent compared to a loss of about 55 percent for an unmodified HVI-PAO at the same viscosity.

Figure 2:
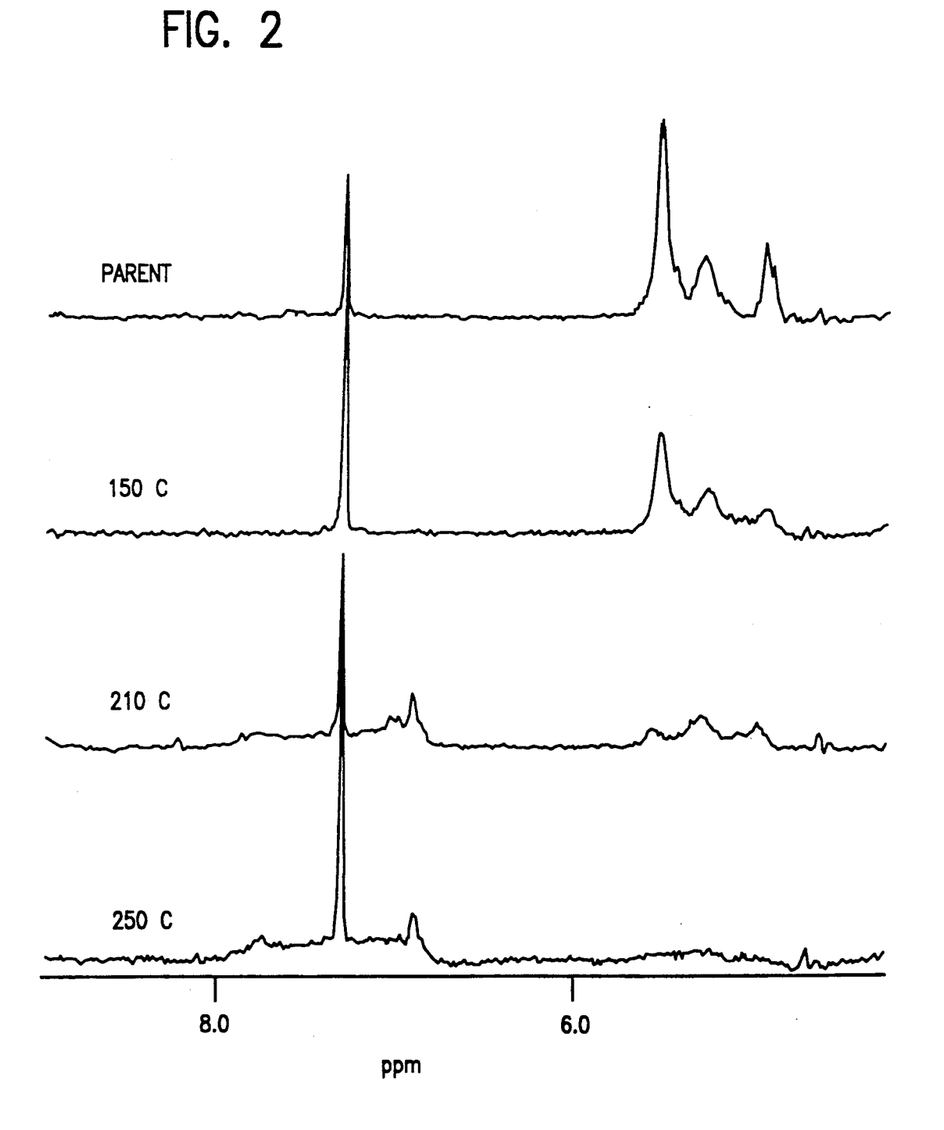
FIG. 2 shows a typical H-nmr spectra for a modified HVI-PAO treated at various reaction temperatures.

FIG. 2 shows a typical H-nmr spectra for a modified HVI-PAO treated at various reaction temperatures. The figure shows the H-nmr (199.55 MHz) spectra for the HVI-PAO (parent) and the reaction products obtained by the reaction of the parent with unreacted decene and dimer over MCM-22 at various temperatures. The figure shows the decrease in olefin protons in the starting material (4.5 to 5.5 ppm) and the increase in aromatic protons (6.4 to 8.5 ppm) as the reaction temperature is raised.

We claim:

1. A process for the preparation of a modified oligomeric reaction product, comprising:
   contacting an alpha-olefin oligomer having a branch ratio of less than 0.19, with an acidic, crystalline zeolite under reaction conditions in the presence of a solid, porous acidic catalyst comprising a crystalline material characterized by an X-ray diffraction pattern including values substantially as set out in Table 1 of the specification, to produce aromatic moieties in the modified oligomeric reaction product.

2. A process according to 1 in which the synthetic porous crystalline material is characterized by an X-ray diffraction pattern including values substantially as set forth in Table 2 of the specification.

3. A process according to 1 in which the synthetic porous crystalline material is characterized by an X-ray diffraction pattern including values substantially as set forth in Table 3 of the specification.

4. A process according to 1 in which the synthetic porous crystalline material is characterized by an X-ray diffraction pattern including values substantially as set forth in Table 4 of the specification.

5. A process according to 1 in which the synthetic porous crystalline material has a composition comprising the molar relationship $$X_2O_3:(n)YO_2,$$

wherein n is at least about 10, X is a trivalent element and Y is a tetravalent element.

6. A process according to 1 in which the synthetic porous crystalline material has the structure of MCM-22.

7. A process according to claim 1 in which the alpha-olefin oligomer is formed by the oligomerization of a 1-olefin in the presence of a reduced valence state metal catalyst.

8. A process according to claim 1 in which the alpha-olefin oligomer comprises the oligomerization product of the oligomerization of a $C_2$-$C_{20}$ 1-alkene in contact with supported reduced metal oxide oligomerization catalyst comprising a lower valence state form of at least Group VIB metal.

9. A process according to claim 8 in which the supported reduced metal oxide catalyst comprises reduced chromium oxide on silica support.

10. A process according to claim 9 in which the oligomerization conditions comprise a temperature between 90° and 250° C.

11. A process according to claim 9 in which the viscosity of the olefin oligomer is from 1.5 to 100 cS at 100° C.

12. A process according to claim 9 in which the olefin oligomer comprises a $C_{30}$ to $C_{1000}$ oligomer having a viscosity of up to 1000 cS at 100° C.

13. A process according to claim 1 in which the reaction conditions include a temperature from about 150° to about 350° C.

14. A process according to claim 13 in which the reaction conditions include a temperature from about 200° to about 300° C.

15. A process according to claim 1 in which the oligomer is present in admixture with unoligomerized olefins and olefin dimers.

16. A process for the preparation of a modified oligomeric reaction product, comprising:
oligomerizing a $C_2$–$C_{20}$ 1-alkene in the presence of a supported reduced metal oxide oligomerization catalyst comprising a lower valence state form of at least one Group VIB metal to form an olefin oligomer having a branch ratio of less than 0.19,
contacting the oligomer with an acidic, crystalline zeolite catalyst comprising zeolite MCM-22 at a temperature from 150° to 400° C. to produce a modified oligomer product of improved stability.

17. A process according to claim 16 in which the oligomer is contacted with the catalyst for a time sufficient to produce aromatic moieties in the modified oligomer reaction product.

18. A process according to claim 16 in which the oligomer is contacted with the catalyst at a temperature from about 100° to about 350° C.

19. A process according to claim 16 in which the oligomer is contacted with the catalyst at a temperature from about 200° to about 300° C.

20. A process according to claim 16 in which the oligomer is present in admixture with unoligomerized alkane and olefin dimer produced during the oligomerization.

21. A process for the preparation of a modified oligomeric reaction product, comprising:
oligomerizing a $C_2$-$C_{20}$ 1-alkene in the presence of a supported reduced metal oxide oligomerization catalyst comprising a lower valence state form of at least one Group VIB metal to form an olefin oligomer having a branch ratio of less than 0.19,
contacting the oligomer with an acidic catalyst at a temperature from 150° to 400° C. to effect cracking of a portion of the oligomer to form cracking fragments and to aromatize the fragments to form aromatics which are alkylated by the oligomer to incorporate an aromatic function into the oligomer to produce a modified oligomer product of improved stability.

22. A process according to claim 21 in which the oligomer is contacted with the catalyst at a temperature from about 100° to about 350° C.

23. A process according to claim 21 in which the oligomer is contacted with the catalyst at a temperature from about 200° to about 300° C.

24. A process according to claim 21 in which the oligomer is present in admixture with unoligomerized alkane and olefin dimer produced during the oligomerization.

25. A process according to claim 21 in which the supported reduced metal oxide catalyst comprises reduced chromium oxide on silica support.

* * * * *